United States Patent
Uto et al.

(10) Patent No.: US 8,482,728 B2
(45) Date of Patent: Jul. 9, 2013

(54) APPARATUS AND METHOD FOR INSPECTING DEFECT ON OBJECT SURFACE

(75) Inventors: Sachio Uto, Yokohama (JP); Hidetoshi Nishiyama, Hitachinaka (JP); Minori Noguchi, Joso (JP)

(73) Assignee: Hitachi High-Technologies Corporation, Tokyo (JP)

(*) Notice: Subject to any disclaimer, the term of this patent is extended or adjusted under 35 U.S.C. 154(b) by 556 days.

(21) Appl. No.: 12/244,958

(22) Filed: Oct. 3, 2008

(65) Prior Publication Data

US 2009/0103079 A1 Apr. 23, 2009

(30) Foreign Application Priority Data

Oct. 4, 2007 (JP) ................................ 2007-261311

(51) Int. Cl.
*G01N 21/00* (2006.01)
(52) U.S. Cl.
USPC ........................................................ 356/237.4
(58) Field of Classification Search
None
See application file for complete search history.

(56) References Cited

U.S. PATENT DOCUMENTS

| | | | |
|---|---|---|---|
| 6,475,353 B1* | 11/2002 | Lantsman | 204/192.12 |
| 6,774,991 B1* | 8/2004 | Danko | 356/237.4 |
| 7,227,628 B1* | 6/2007 | Sullivan et al. | 356/237.4 |
| 2004/0012775 A1* | 1/2004 | Kinney et al. | 356/237.2 |
| 2004/0042877 A1* | 3/2004 | Somekh et al. | 356/237.5 |
| 2005/0213086 A1* | 9/2005 | Hamamatsu et al. | 356/237.2 |
| 2006/0158823 A1* | 7/2006 | Mizuno et al. | 361/234 |
| 2006/0213537 A1* | 9/2006 | Atalla | 134/18 |
| 2007/0188745 A1* | 8/2007 | Smedt | 356/237.2 |
| 2009/0009763 A1* | 1/2009 | Zangooie et al. | 356/601 |
| 2009/0056761 A1* | 3/2009 | Au et al. | 134/21 |

FOREIGN PATENT DOCUMENTS

| | | |
|---|---|---|
| JP | 62-089336 | 4/1987 |
| JP | 06-224105 A | 8/1994 |
| JP | 07-039787 A | 2/1995 |
| JP | 7311157 A | 11/1995 |

(Continued)

OTHER PUBLICATIONS

Japanese Office Action, and English translation thereof, issued in Japanese Patent Application No. 2008-256945 dated Jun. 26, 2012.

(Continued)

*Primary Examiner* — Gregory J Toatley
*Assistant Examiner* — Juan D Valentin, II
(74) *Attorney, Agent, or Firm* — McDermott Will & Emery LLP

(57) ABSTRACT

An aspect of the invention provides a defect inspection apparatus being able to accurately inspect a micro foreign matter or defect at a high speed for an inspection target substrate in which a repetitive pattern and a non-repetitive pattern are mixed. In a foreign matter anti-adhesive means 180, a transparent plate 187 is placed on a placement table 34 through a frame 185. In the foreign matter anti-adhesive means 180, a shaft 181 which is rotatably supported by two columnar supports 184 fixed onto a base 186 is coupled to a motor 182 by a coupling 183. The shaft 181 is inserted into a part of a frame 185 between the two columnar supports 184 such that the frame 185 and the transparent plate 187 are turnable about the shaft 181. Therefore, the whole of the frame 185 is opened and closed in a Z-direction about the shaft 181, and a wafer 1 on the placement table 34 can be covered with the frame 185 and the transparent plate 187.

22 Claims, 12 Drawing Sheets

FOREIGN PATENT DOCUMENTS

| | | |
|---|---|---|
| JP | 2000-019717 A | 1/2000 |
| JP | 2001-060607 | 3/2001 |
| JP | 2002082056 A | 3/2002 |
| JP | 2004-063923 A | 2/2004 |
| JP | 2004-327546 A | 11/2004 |

OTHER PUBLICATIONS

Japanese Office Action, and partial English translation thereof, issued in Japanese Patent Application No. 2008-256945 dated Sep. 4, 2012.

* cited by examiner

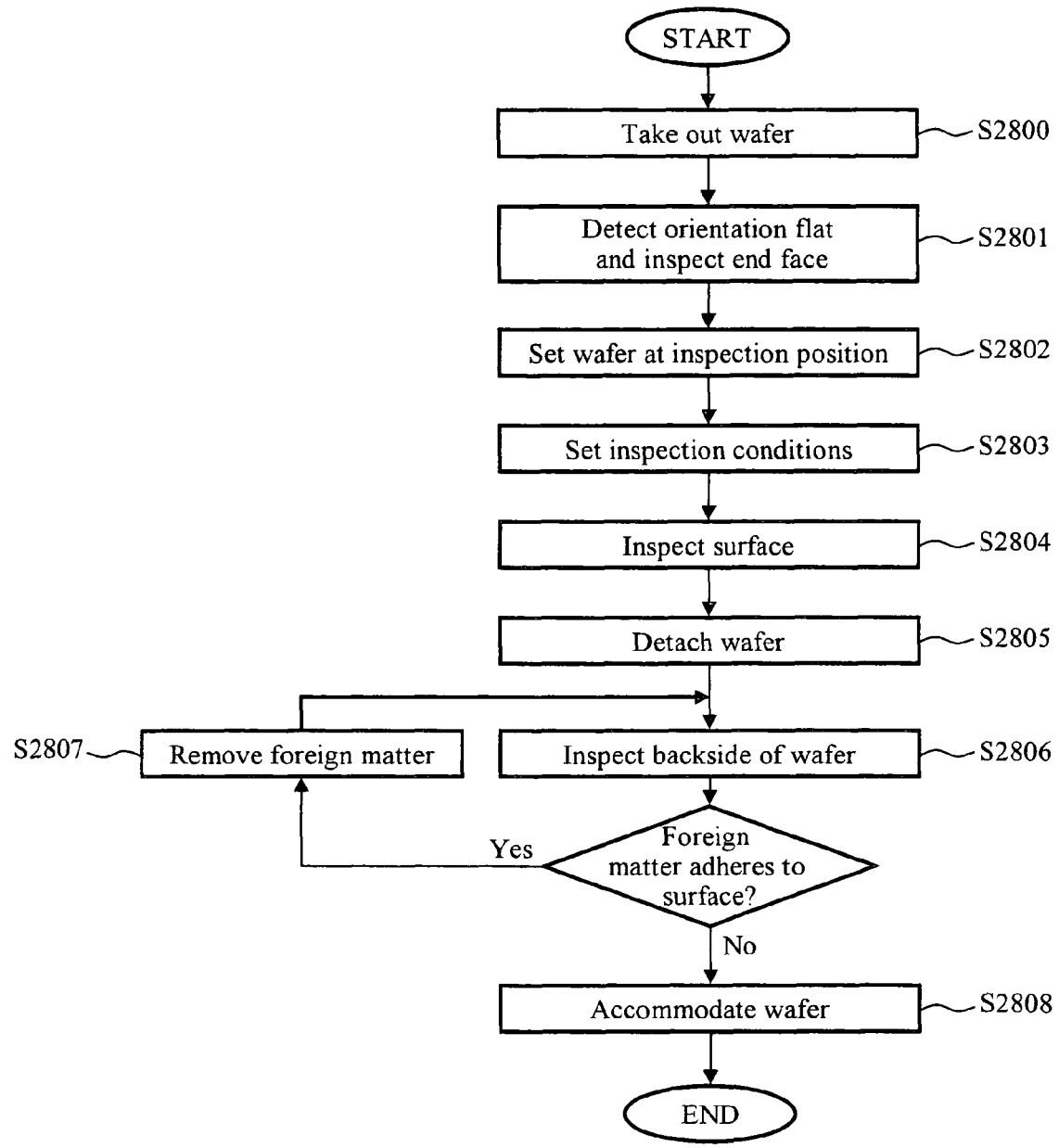

APPARATUS AND METHOD FOR INSPECTING DEFECT ON OBJECT SURFACE

BACKGROUND OF THE INVENTION

1. Field of the Invention

The present invention relates to an apparatus and a method for inspecting a defect in an object surface, in which a foreign matter existing in a thin film substrate, a semiconductor substrate, and a photomask or the defect generated in a circuit pattern is detected in producing a semiconductor chip or a liquid crystal product.

2. Description of the Related Art

In a semiconductor production process, existence of the foreign matter on the semiconductor substrate (wafer) causes an insulation failure or a short circuit of an interconnection. As a process of a semiconductor element is moved to a finer design rule, a finer foreign matter causes an insulation failure of a capacitor or a breakage of a gate oxide film or the like. The foreign matters are generated in various states from various factors such as a moving part of a conveyance apparatus, a human body, reaction of a process gas in a treatment apparatus, and an impurity of a chemical or a material.

Similarly, in a liquid crystal display element production process, the liquid crystal display element is spoiled when a pattern defect is generated by the foreign matter. Similarly, in the printed circuit board production process, the mixing of foreign matter causes the short circuit and connection failure of the pattern.

Therefore, in the semiconductor production, a foreign matter inspection apparatus or a plurality of foreign matter inspection apparatuses in some cases is disposed in each production line, and early detection of the foreign matter is fed back to the production process to enhance a yield of the semiconductor production.

For example, Japanese Patent Application Laid-Open (JP-A) No. 62-89336 discloses a technique of detecting the foreign matter on the semiconductor substrate, wherein the semiconductor substrate is irradiated with a laser beam to detect scattered light which is generated in the case where the foreign matter adheres onto the semiconductor substrate, and the scattered light is compared to that of the inspection result of the same type semiconductor substrate inspected immediately before, whereby the foreign matter and defect can be inspected with high sensitivity and high reliability while misinformation is eliminated.

JP-A No. 2001-60607 discloses a technique of measuring a foreign matter size.

Because high-speed and high-sensitivity inspection is demanded in the foreign matter inspection apparatus, speed enhancement of a wafer moving stage, high NA and high resolution of a detection optical system becomes significant in development on the inspection apparatus. It is also necessary to prevent not only the generation of dust from the inspection apparatus per se but also adhesion of the new foreign matter to an inspection target during the inspection.

However, even if cleanness in the inspection apparatus is improved to prevent the generation of dust, because of the existence of the moving part such as the conveyance unit, it is substantially difficult to make an expensive atmosphere in which the foreign matter is completely removed.

In the technique disclosed in JP-A No. 62-89336, the micro foreign matter or defect on the substrate in which a repetitive pattern and a non-repetitive pattern coexist cannot easily be detected with high sensitivity and at a high speed. That is, there is a problem in that detection sensitivity (minimum detectable foreign matter size) is lowered in portions except for the repetitive pattern portion such as a memory cell portion.

Additionally, in the technique disclosed in JP-A No. 62-89336, there is a problem in that the detection sensitivity is lowered for the micro foreign matter or defect having a level of 0.1 µm in an area where pattern density is high.

Additionally, in the technique disclosed in JP-A No. 62-89336, there is a problem in that the detection sensitivity is lowered for a thin-film-like foreign matter or the foreign matter and defect which cause the short circuit between interconnections.

In the technique disclosed in JP-A No. 2001-60607, there is a problem in that measurement accuracy is lowered for the foreign matter or defect. Additionally, there is a problem in that the detection sensitivity is lowered for the foreign matter on a wafer surface in which a transparent thin film is formed.

An object of the invention is to realize the defect inspection method and apparatus being able to accurately inspect the micro foreign matter or defect at a high speed for the inspection target substrate in which the repetitive pattern and the non-repetitive pattern are mixed.

SUMMARY OF THE INVENTION

In order to achieve the object, the invention is configured as follows.

In accordance with a first aspect of the invention, there are provided a defect inspection apparatus and a defect inspection method both of which irradiate a surface of a sample placed on a placement table with light and detect light reflected from the sample surface to detect a defect on the sample surface, wherein the defect of the sample surface is detected by irradiating the sample surface with the light, while a foreign matter anti-adhesive means prevents a foreign matter from adhering to the surface of the sample placed on the placement table.

In accordance with a second aspect of the invention, a defect inspection apparatus includes a light source; a placement table on which a sample is placed; an irradiation means which irradiates the sample placed on the placement table with light emitted from the light source; a light detection means which detects light reflected from a sample surface; a defect detection means which detects a defect on the sample surface based on the reflected light detected by the light detection means; and a backside foreign matter inspection means which inspects whether or not a foreign matter is adhering to the backside of the sample.

In the defect inspection apparatus according to the second aspect of the invention, preferably the foreign matter anti-adhesive means for preventing a foreign matter from adhering to the surface of the sample placed on the placement table includes a transparent plate which transmits the light; and a drive means which movably supports and moves the transparent plate toward above and from above the surface of the sample placed on the placement table.

Accordingly, the invention can realize the defect inspection method and apparatus being able to accurately inspect the micro foreign matter or defect at a high speed for the inspection target substrate in which the repetitive pattern and the non-repetitive pattern are mixed.

BRIEF DESCRIPTION OF THE DRAWINGS

FIG. 9 is a flowchart explaining an inspection procedure of the first embodiment;

Figure 1:
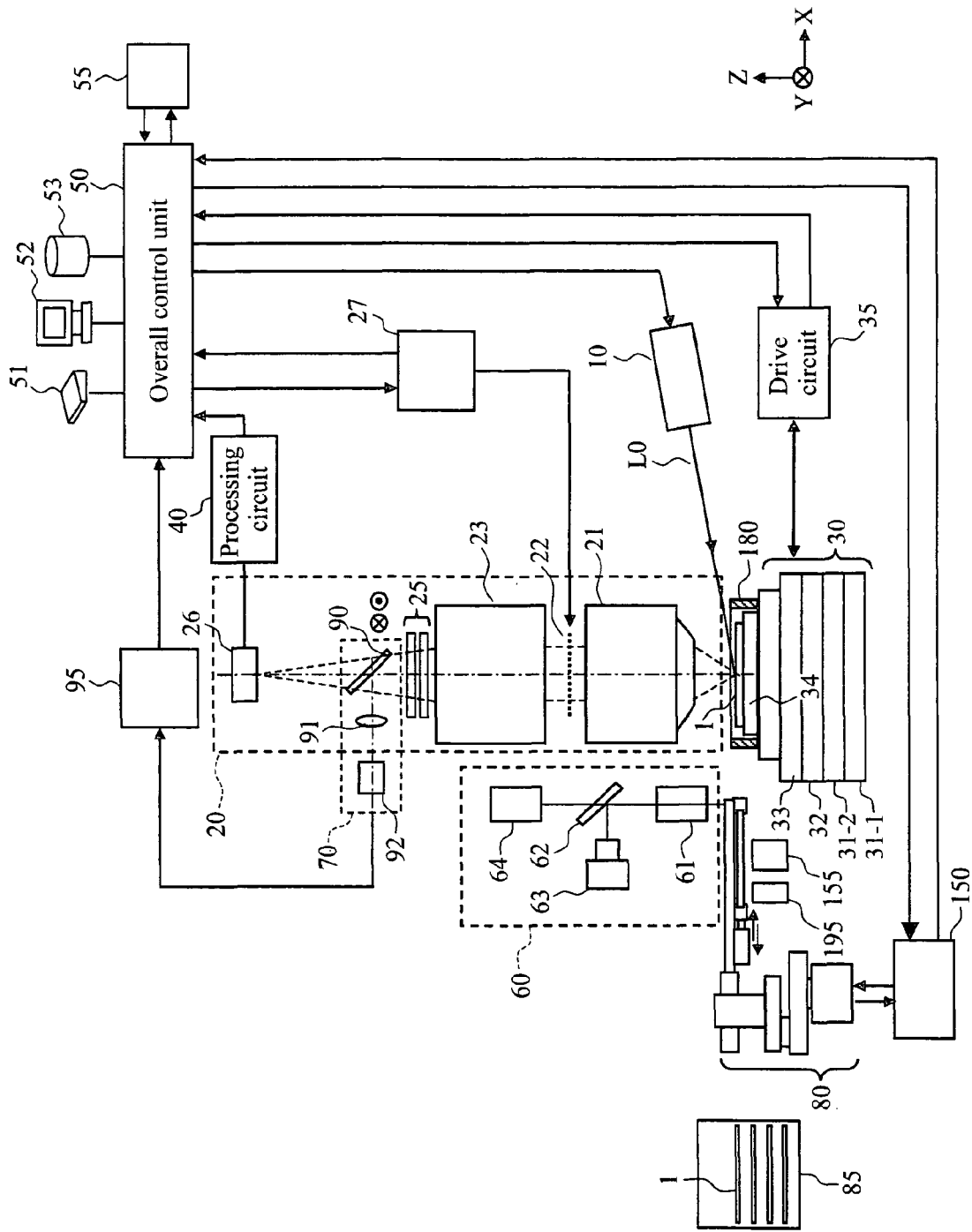
FIG. 1 is a schematic diagram showing a configuration of a defect inspection apparatus according to a first embodiment of the invention.

DESCRIPTION OF REFERENCE NUMERALS 1 wafer (inspection target substrate)
10 illumination optical system
11 laser beam source
20 detection optical system
25 optical filter
30 conveyance system
35 drive circuit
40 signal processing circuit
50 overall control unit
51 input means
52 display means
53 storage means
60 observation optical system
70 pupil observation optical system
80 conveyance robot
82 conveyance arm
155 backside foreign matter inspection apparatus
180 foreign matter anti-adhesive means
195 foreign matter removal means
300 end-face inspection apparatus
350 orientation flat detection optical system
1301 A/D converter
1302 data storage unit
1303 threshold computation processing unit
1307 foreign matter detection processing circuit
1308 inspection area processing unit
1309 feature value computation circuit (feature value computation unit)
1310 feature value integrated processing unit

DETAILED DESCRIPTION OF THE INVENTION

Exemplary embodiments of the invention will be described below with reference to the drawings.

A defect inspection apparatus according to embodiments of the invention accurately inspects various defects such as a foreign matter, a pattern defect, or a micro scratch on various inspection substrates such as a wafer in various kinds and various production processes at a high speed, and particularly the defect inspection apparatus stably detects a defect on a thin-film surface formed in a wafer surface while the defect on the thin-film surface is separated from a defect inside the thin film. The defect inspection apparatus of the embodiments has a configuration in which the surface of the wafer which is of the inspection target is not contaminated by particles such as dust or foreign matters in the apparatus.

That is, in the defect inspection apparatus of the embodiments, a foreign matter anti-adhesive means which has a transparent portion is provided above the wafer, contaminants such as the foreign matter and the particles suspended in the inspection apparatus are prevented from directly dropping on the surface of the wafer. Additionally, the defect inspection apparatus includes a means which checks a contamination state of a backside of the wafer 1 by inspecting the backside of the wafer placed on the placement table for the purpose of inspection in a conveyance path. Additionally, the defect inspection apparatus according to the embodiments of the invention includes a means which cleans the backside of the wafer according to the contamination result. The placement table is also replaced according to the contamination result of the backside of the wafer.

The defect inspection apparatus of the embodiments will specifically be described below. In the following embodiments, such defects as small and large foreign matters and micro scratches on both a semiconductor wafer and on a transparent film formed on the wafer, and as foreign matters and pattern defects inside the transparent film, are inspected. However, the invention is not limited to the semiconductor wafer, but the invention can also be applied to a thin-film substrate, a photomask, TFT, PDP, and the like.

First Embodiment

FIG. 1 is a schematic diagram showing a configuration of an object surface defect inspection apparatus according to a first embodiment of the invention. Referring to FIG. 1, the defect inspection apparatus mainly includes an illumination optical system 10, a variable magnification detection optical system 20, a conveyance system 30, a signal processing system 40, and an overall control unit 50 which controls the whole of the defect inspection apparatus.

Figure 2A:
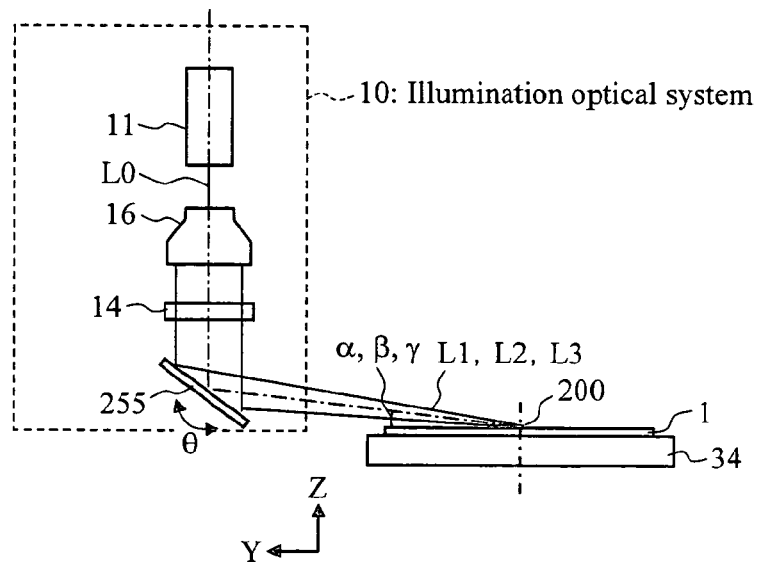
FIG. 2A shows an alignment of an illumination optical system.

The conveyance system 30 includes an X-stage 31-1, a Y-stage 31-2, a Z-stage 32, a theta stage 33, and a drive circuit 35 for control thereof. The X-stage 31-1, the Y-stage 31-2, the Z-stage 32, and the theta stage 33 move an inspection target substrate 1 such as various kinds of wafers obtained from various production processes, with placing the substrate 1 on a placement table 34. As shown in FIG. 2A, the illumination optical system 10 includes a laser beam source 11, a beam expanding optical system 16, mirrors 260 to 268, lenses 231 to 233, and wave plates 211 to 213. The illumination optical system 10 illuminates a surface of the wafer 1 from plural oblique directions with light emitted from the laser beam source 11 through the mirrors 260 to 268, the wave plates 211 to 213, and the lenses 231 to 233 after the light expanded with the beam expanding optical system 16.

In FIG. 1, the detection optical system 20 includes an objective lens 21, a spatial filter 22, an imaging lens 23, an optical filter 25, a beam splitter 90, and a photodetector 26 such as a TDI image sensor.

The signal processing circuit 40 detects the defect and the foreign matter by processing an image signal detected by the photodetector 26.

The observation optical system 60 includes a lens 61, a half mirror 62, an illumination light source 63, and an imaging means 64. In the observation optical system 60, light emitted from the illumination light source 63 is reflected by the half mirror 62 to bend its optical path toward the wafer 1, and the surface of the wafer 1 is illuminated with the light collected by the lens 61. Of the light which is reflected and scattered by the wafer 1, the light incident to the lens 61 is transmitted through the half mirror 62, and an image is formed on a light acceptance surface of the imaging means 64. The observation optical system 60 confirms existence and a shape of the foreign matter based on inspection result which is obtained by inspecting the wafer 1 with the variable magnification detection optical system 20.

The overall control unit 50 sets an inspection condition and the like to control the illumination optical system 10, the variable magnification detection optical system 20, the conveyance system 30, and the signal processing system 40 as a whole. The overall control unit 50 includes an input and output means 51 (including a keyboard and a network), a display means 52, and a storage means 53. Pieces of design data such as a circuit pattern formed in the surface of the inspection target substrate 1 are stored in a storage means (server) 55, and a spatial optical image can be formed from the design data.

The foreign matter inspection apparatus is also includes an automatic focus control system (not shown) such that the image of the surface of the wafer 1 is formed on the light acceptance surface of the photodetector 26.

In the defect inspection apparatus, the surface of the inspection target substrate 1 can be illuminated from the plural directions.

As shown in FIG. 2A, the illumination optical system 10 includes the beam expanding optical system 16, the lens 14, the mirror 255 and the like. The beam expanding optical system 16 includes a concave lens (not shown), a convex lens (not shown) and the like. The lens 14 shapes the light into a slit-like beam. The illumination optical system 10 shapes light L0 emitted from the laser beam source 11 into a slit-like (linear) beam 200 to form a slit-like illumination area 201 (FIG. 2C) in the wafer 1.

Figure 2B:
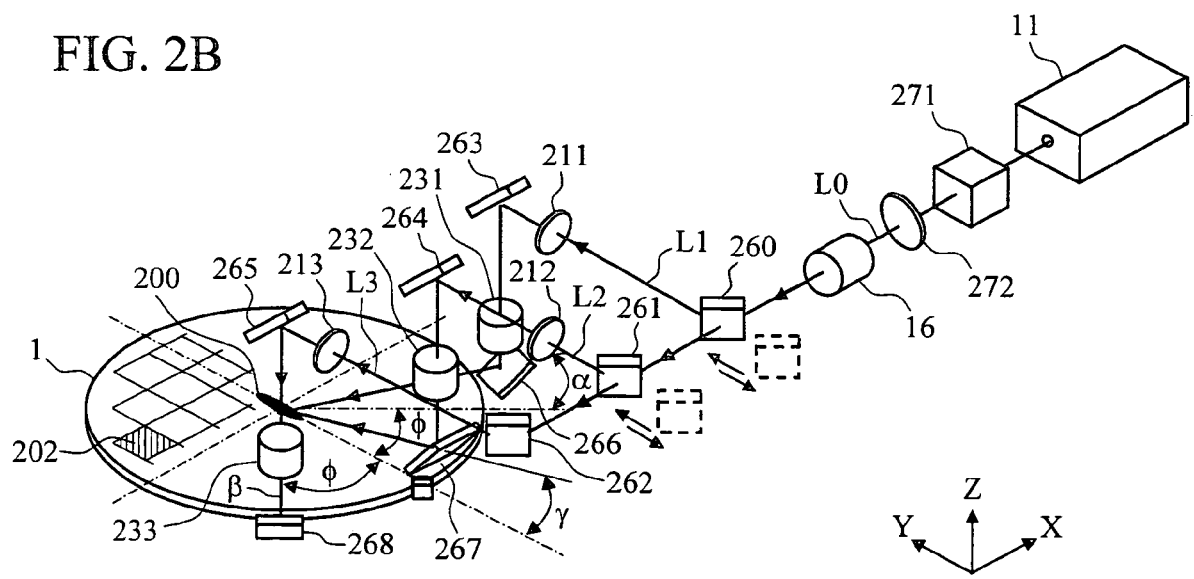
FIG. 2B show a schematic configuration of a low-angle illumination optical system.

In the inspection apparatus of the first embodiment, in order to illuminate the surface of the wafer 1 at a low angle (low incident angle) with a laser beam having a single wavelength, the wafer 1 placed on a sample placement table (wafer chuck 34) is irradiated in a planar manner from plural directions (illumination directions of laser beams L1, L2, and L3 in FIG. 2B) and at plural illumination angles (α, β, and γ in FIG. 2B) with the slit-like beam 200 (with which the slit-like illumination area 201 of the wafer 1 is irradiated, hereinafter referred to as slit-like beam) as shown in FIG. 2B.

The reason why the illumination light is shaped into the slit-like beam 200 is that the image of the scattered light from the foreign matter or defect, generated by the illumination, is formed on detection surfaces of the light acceptance elements arranged in line in the photodetector 26 and collectively detected to achieve the speed enhancement of the foreign matter inspection.

That is, the theta stage 33 is driven to adjust an orientation of the wafer 1 placed on the placement table 34 such that an array direction of chips 202 formed on the wafer 1 is parallel to a scanning direction of the X-stage 31-1 and a scanning direction of the Y-stage 31-2, and the wafer 1 whose orientation is adjusted is irradiated with the slit-like beam 200.

In the shape of the slit-like illumination area 201 on the wafer 1 irradiated with the slit-like beam 200, using an optical system in which the light is collected in the X-direction to become parallel to the Y-direction, an optical axis is adjusted so as to be orthogonal to a scanning direction X of the X-stage 31-1 (a lengthwise direction of the slit-like illumination area 201 on the wafer 1 is orthogonal to the scanning direction X of the X-stage 31-1), so as to be parallel to a scanning direction Y of the Y-stage 31-2 (the lengthwise direction of the slit-like illumination area 201 on the wafer 1 is parallel to the scanning direction Y of the Y-stage 31-2), and so as to be parallel to a pixel array direction of the photodetector 26.

Figure 3A:
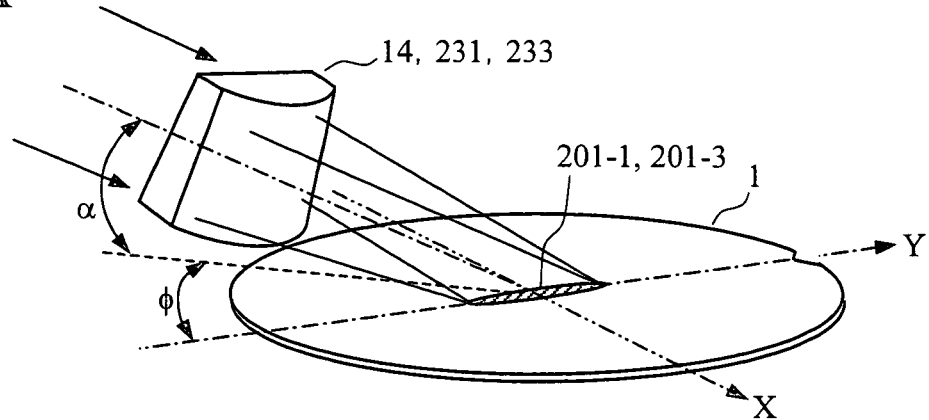
FIG. 3A is a perspective view showing a conical surface lens, which is used in the illumination optical system.
Figure 3B:
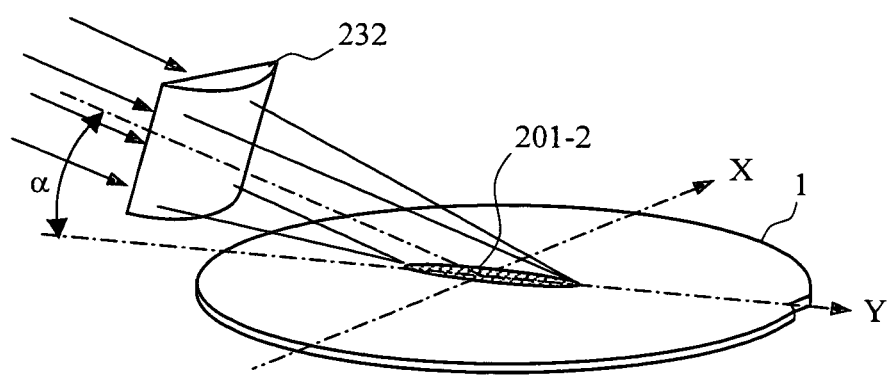
FIG. 3B is a perspective view showing a cylindrical lens, which is used in the illumination optical system.

This is because alignment between the chips can be easily performed when image signals of the chips are compared to each other. As shown in FIGS. 3A and 3B, the slit-like illumination area 201 can be formed by providing a conical surface lens 14 or a cylindrical lens in an optical path.

For example, as shown in FIG. 3A, lenses 231 and 233 are formed of conical surface lenses in which a curvature radius is continuously changed in the lengthwise direction, and a major axis of the slit-like beam 200 with which the wafer 1 is irradiated from a direction of an angle θ relative to a horizontal direction becomes parallel to the scanning direction of the Y-stage 31-2.

In the illumination with the laser beams L1 and L3, the wafer 1 is irradiated with the slit-like laser beams from their respective directions each of which is rotated right or left by the angle φ with respect to the Y-axis direction of the wafer 1 and inclined by an angle α toward a Z-axis direction (in FIG. 2B, both an optical path in which illumination light from the laser beam L3 is reflected by the mirror 265 and transmitted through the lens 233 to the mirror 268 and an optical path from the mirror 268 to the illumination area 201 of the slit-like beam 200 of the wafer 1 are shown while overlapped with each other).

In the illumination from the laser beam L2, in order to illuminate the wafer 1 from the same direction as the scanning direction of the Y-stage 31-2, the slit-like beam 200 can be formed by the cylindrical lens 232 of FIG. 3B to irradiate the slit-like area 201-1 on the wafer 1 therewith (although the cylindrical lens 232 is disposed perpendicular to the optical axis (dashed-dotted line in FIG. 3B) in FIG. 3B, actually the cylindrical lens 232 is disposed while inclined in the Y-direction with respect to the optical axis in order to correct a shift of a focal point in irradiating the wafer 1 with the slit-like beam 200).

As shown in FIG. 2A, an angle θ of the mirror 255 is changed by a pulse motor (not shown) in response to an instruction provided from the overall control unit 50, whereby the illumination angles (α, β, and γ) can be changed according to the kind of the foreign matter which is of the inspection object on the inspection target substrate 1.

Figure 2C:
FIG. 2C show a relationship between an illumination area and a detection area in the first embodiment.

As shown in FIG. 2C, in the case of any illumination angle, the slit-like area 201 on the wafer 1 irradiated with the slit-like beam 200 covers a pixel array direction 203 of the photodetector 26. In the illumination from each of the laser beams L1, L2, and L3, an illumination position of the slit-like beam 200 is matched with the slit-like areas 201-1 to 201-3 on the wafer 1.

Therefore, the illumination having the parallel light in the Y-direction and the azimuth angle φ near 45 degrees can be realized. Particularly, the slit-like beam 201 is parallel to the Y-direction, whereby the diffraction light from the circuit pattern in which main line group is orientated toward the X-direction and Y-direction is obstructed by the spatial filter 22.

As shown in FIG. 1, in the optical path of the detection optical system 20, the spatial filter 22 is adjusted such that bright spots of the diffraction light image reflected from the repetitive pattern at an image formation position of Fourier transform are taken with a pupil observation optical system 70, and such that the bright spots is obstructed by a light shielding plate having a rectangular light shielding portion provided at the image formation position of the Fourier transform. The pupil observation optical system 70 includes a mirror 90 which can be retracted in the X-direction during the inspection, a projection lens 91, and a TV camera 92.

These operations are performed based on the instruction from the overall control unit 50. For example, the inspection is performed at a high-sensitivity inspection mode with high magnification when the circuit pattern formed on the inspection target substrate 1 has a high density, and high-speed inspection is performed with low magnification when the circuit pattern has a low density. That is, the magnification is set according to both the information on the surface of the inspection target substrate 1 placed on the stage and the production process such that the micro defects are detected as much as possible.

For example, high-output YAG laser having a wavelength of 532 nm of a second harmonic or a wavelength of 266 nm of a fourth harmonic can be used as the laser beam source 11. Alternatively, an ultraviolet laser, a far ultraviolet laser, a vacuum ultraviolet laser may be used as the laser beam source 11. The light sources such as an Ar laser, a nitrogen laser, a He—Cd laser, an excimer laser, and a semiconductor laser light source may also be used as the laser beam source 11.

Generally, the wavelength of the laser beam is shortened to improve the resolution of the detected image, which allows highly-sensitive inspection.

Figure 4:
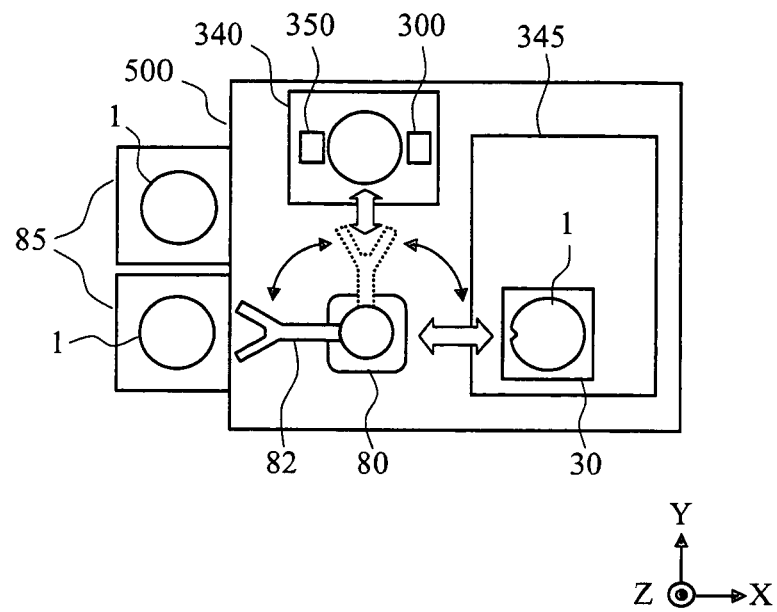
FIG. 4 is a view explaining an operation of the defect inspection apparatus of the first embodiment.

An example of the operation of the object surface defect inspection of the first embodiment will be described below with reference to FIG. 4. In FIG. 4, a defect inspection apparatus 500 includes a wafer cassette 85 in which wafers 1 are accommodated, a conveyance robot 80, a conveyance arm 82 which conveys the wafer while seizing the wafer 1, an orientation flat detection unit 340 which detects an orientation flat of the wafer 1, an orientation flat detection optical system 350, an end-face inspection apparatus 300 which detects a defect of an edge portion of the wafer 1, and a defect detection device 345 which detects the defect in the surface of the wafer 1.

The wafer 1 which is of the inspection target substrate is taken out from the wafer cassette 85 and conveyed to the orientation flat detection unit 340 by the conveyance arm 82.

Figure 5:
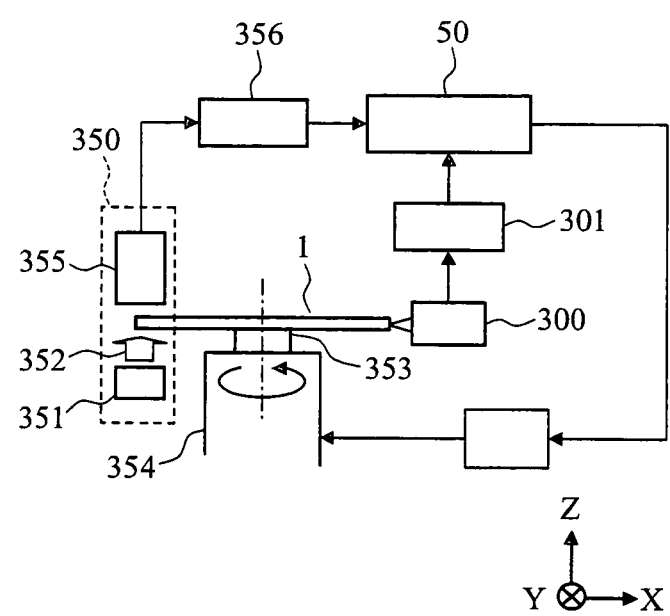
FIG. 5 is a side view showing arrangements of an orientation flat detection optical system and an end-face inspection apparatus.

FIG. 5 is a sectional view showing the orientation flat detection unit 340 when viewed from the y-direction of FIG. 4. In FIG. 5, the wafer 1 is vacuum-adsorbed by a chuck 353 and rotated by a motor 354. The orientation flat detection optical system 350 includes a floodlight unit 351 and a detection unit 355. Illumination light 352 is accepted from the floodlight unit 351, and a light acceptance signal of the detection unit 355 is transmitted to the overall control unit 50 through a processing circuit 356.

The overall control unit 50 computes an eccentric amount of the wafer 1 and an orientation flat (V-notch) position, and transmits a signal for correcting an orientation flat position with respect to a Y-axis to the motor 354 through a controller 357. The eccentric amount is fed back as a correction value to a movement value of the conveyance arm 82 when the conveyance robot 80 places the wafer 1 on the conveyance system 30 of the defect detection device 345, thereby positioning the wafer 1 at the center of the placement table 34 of the defect inspection apparatus 345.

On the other hand, while the wafer 1 is rotated, the end-face inspection apparatus 300 inspects the defect in the end-face portion (edge portion) of the wafer 1. The detected signal is processed by the processing circuit 301, and a defect signal is transmitted to the overall control unit 50. When the defect is detected, a coordinate position in a rotating direction is stored in the overall control unit 50 from a pulse count of a rotary encoder (not shown) coupled to the motor 354 based on the orientation flat position which is of an origin position.

Thus, the fine defect on the surface of the wafer 1 can be inspected at a high speed by the defect inspection apparatus having the configuration mentioned above.

By the way, various defects exist in the surface of the wafer 1 placed on the placement table 34 of the defect inspection apparatus 345, and it is necessary that the defect inspection apparatus 345 detects many kinds of defects as many as possible. Therefore, it is necessary to set inspection conditions according to the kind of defect to be detected.

In the defect inspection apparatus 345 of the first embodiment, the direction and angle of the illumination can be changed according to the kind of the defect. Therefore, the illumination optical system 10 includes a drive mechanism which drives the mirror and the lens. In many cases, because the optical system is placed above the wafer 1, it is difficult to completely eliminate particle contamination, such as the generation of dust from the drive portion of the mirror and lens, on the surface of the wafer 1, from the dust or foreign matter in the inspection apparatus.

Figure 6A:
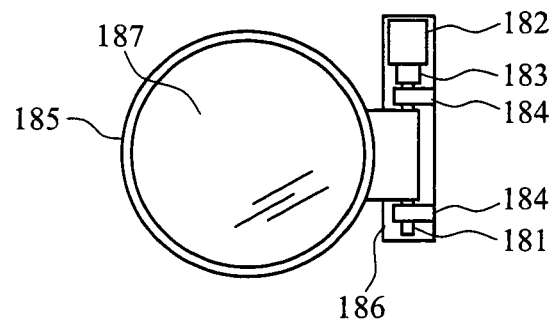
FIGS. 6A and 6B are views explaining a configuration of a foreign matter anti-adhesive means of the first embodiment.
Figure 6B:
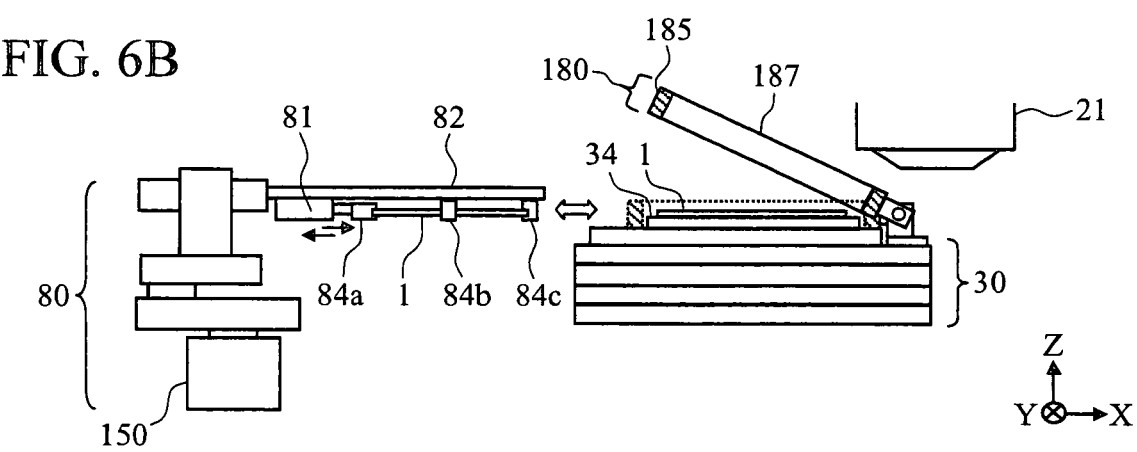

Therefore, as shown in FIGS. 6A and 6B, in the first embodiment, a foreign matter anti-adhesive means 180 is disposed above the inspection target substrate 1 to prevent the contamination particles such as the dust and the foreign matter from directly adhering to the surface of the wafer 1. FIG. 6A is a plan view of the foreign matter anti-adhesive means 180, and FIG. 6B is a side view of the foreign matter anti-adhesive means 180.

In the foreign matter anti-adhesive means 180, a transparent plate 187 is placed above the placement table 34 by a frame 185. In the foreign matter anti-adhesive means 180, a shaft 181 is rotatably supported by (or inserted into) two columnar supports 184 fixed onto a base 186, and the shaft 181 is coupled to a motor 182 by a coupling 183. The shaft 181 is inserted into a part of the frame 185 between the columnar supports 184, and the frame 185 and the transparent plate 187 can be turned about the shaft 181. That is, the whole of the frame 185 is opened and closed in the Z-direction about the shaft 181, and the wafer 1 of the placement table 34 can be covered with the frame 185 and the transparent plate 187.

A procedure in which the conveyance arm 82 places the wafer 1 onto the placement table 34 of the conveyance unit 30 in the defect inspection apparatus 345 will be described below.

In the placement of the wafer 1 on the placement table 34, the placement table 34 is moved to and waits ready at a position in the X-direction away from the optical axis of the objective lens 21 of the detection optical system 20 by the conveyance system 30. Then, the motor 182 is driven to turn the foreign matter anti-adhesive means 180 by a drive signal (not shown) supplied from the overall control unit 50, and the foreign matter anti-adhesive means 180 is opened such that the wafer 1 can be conveyed onto the placement table 34.

While an end portion of the wafer 1 is retained by a pawl 84 (84a to 84c) which is provided in an openable and closable manner in the conveyance arm 82, the wafer 1 is moved in the X-direction of FIG. 6B and placed on the placement table 34. The pawl 84 retains the wafer 1 from three directions of its circumference, and the pawl 84 (84a to 84c) is radially movable from the center of the wafer 1 toward the circumference by a mechanism (not shown) driven by an actuator 81, thereby grasping and releasing the end portions of the wafer 1.

After the wafer 1 is placed on the placement table 34, the foreign matter anti-adhesive unit 180 is turned by the motor 182 to cover the wafer 1. At this point, the defect inspection is performed in the surface of the wafer 1.

A material (such as nitrocellulose) and a thickness which do not have an influence on the image formation when being provided in the optical path of the detection optical system 20, are selected as the transparent plate 187. For example, a plane parallel plate and a Pericles film can be used as the transparent plate 187. When the transparent plate 187 is provided at a position away from the inspection surface of the wafer 1, the micro foreign matter on the transparent plate 187 becomes out of focus on the detector 26, and the foreign matter is not detected by the detector 26. In the series of operations, the signal is supplied from the overall control unit 50 to the control circuit 150, and the control circuit 150 controls the conveyance robot 80 according to the supplied signal.

Figure 7:
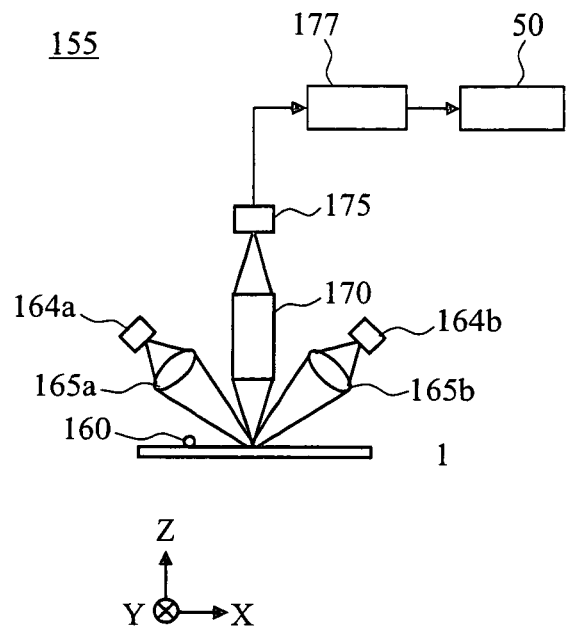
FIG. 7 is a schematic diagram showing a configuration of a backside foreign matter inspection apparatus in the first embodiment.

A configuration of a backside foreign matter inspection apparatus will be described with reference to FIGS. 1 and 7. The backside foreign matter inspection apparatus 155 is provided in a path in which the wafer 1 is taken out from the wafer cassette 85 and placed in the defect inspection apparatus. The backside of the wafer 1 is irradiated with the light emitted from a light source 164 (164a and 164b) through a collective lens 165 (165a and 165b), and the scattered light from the defect and foreign matter is detected by a detector 175 through an imaging lens 170. The imaging lens 170 and the detector 175 are disposed in a direction perpendicular to the wafer 1. A detection signal supplied from the detector 175 is processed by a processing circuit 177, and a defect signal is fed into the overall control unit 50.

For example, the backside foreign matter inspection apparatus 155 has the configuration disclosed in Japanese Patent Application Publication No. 6-41920. The spatial filter ring is eliminated because the circuit pattern does not exist in the backside of the wafer 1. In the inspection with the backside foreign matter inspection apparatus 155, the optical system having a large focal depth is required because the foreign matter having a size of several micrometers is inspected. A positional coordinate of the defect detected by the backside foreign matter inspection apparatus 155 is stored in the overall control unit 50, and the foreign matter is removed by a foreign matter removal means 195 when the overall control unit 50 determines that the foreign matter on backside of the wafer 1 adheres to other wafers 1 stored in the cassette 85 while the wafer 1 being stored therein.

Figure 8:
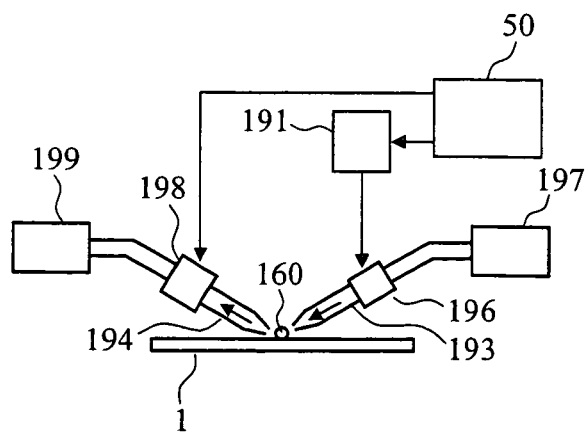
FIG. 8 is a schematic diagram showing a configuration of a foreign matter removal means in the first embodiment.

As shown in FIG. 8, the foreign matter removal means 195 sprays a high-pressure gas to the backside of the wafer 1 from a nozzle 193 according to a pulse signal of an oscillator 191, and a foreign matter 160 adhering to the backside of the wafer 1 is caused to float and sucked by a suction nozzle 194. The numeral 197 designates a high-pressure gas source, and the numeral 199 designates a suction pump. The suction nozzle 194 sucks the foreign matter while the valve 198 is opened. The operations of the valves 196 and 198 are controlled by the overall control unit 50.

An example of an inspection sequence performed by the defect inspection apparatus of the first embodiment will be described below. FIG. 9 is an inspection flow chart showing a series of operations in which the wafer 1 is accommodated in the wafer cassette 85 after the completion of inspection since the wafer 1 has been taken out from the wafer cassette 85 to perform the inspection.

Referring to FIG. 9, the wafer 1 is taken out from the wafer cassette 85 by the conveyance arm 82 (Step S2800). The wafer 1 is conveyed to the orientation flat detection unit 340, the wafer 1 is fixed to the chuck 353 by vacuum adsorption, the wafer 1 is rotated by the motor 354, and the orientation flat detection and the end-face inspection are performed (Step S2801).

The wafer 1 is retained by the conveyance arm 82 again, and the wafer 1 is vacuum-adsorbed to the placement table 34 at the defect inspection position (Step S2802). Pieces of chip layout information such as the chip size of the wafer 1 and the presence or absence of chips on the wafer 1 are set, the array direction of the chips 202 of the wafer 1 is placed in parallel (because the rotational displacement is substantially decreased to zero) to the detector 26 by rotating the whole of the wafer 1. Then, the inspection area, the detection sensitivity in the inspection area, the illumination condition, and the optical conditions such as magnification selection of the detection optical system 20 are set in order to perform the inspection of each area on the wafer 1 with an optimum sensitivity (Step S2803). The inspection of the whole surface of the wafer 1 is started (Step S2804).

Then, the conveyance arm 82 detaches the wafer 1 (Step S2805), the backside inspection is performed to the wafer 1 in the conveyance path (Step S2806), and a determination whether or not the foreign matter exists is made (Step S2806a). In Step S2806a, in the case of the adhesion of the foreign matter which can become problematic in the subsequent processes, the foreign matter is removed (Step S2807). Then, the process returns to Step S2806, the backside inspection is performed again. When the foreign matter does not exist, the wafer 1 is accommodated in the wafer cassette (Step S2808).

Figure 12:
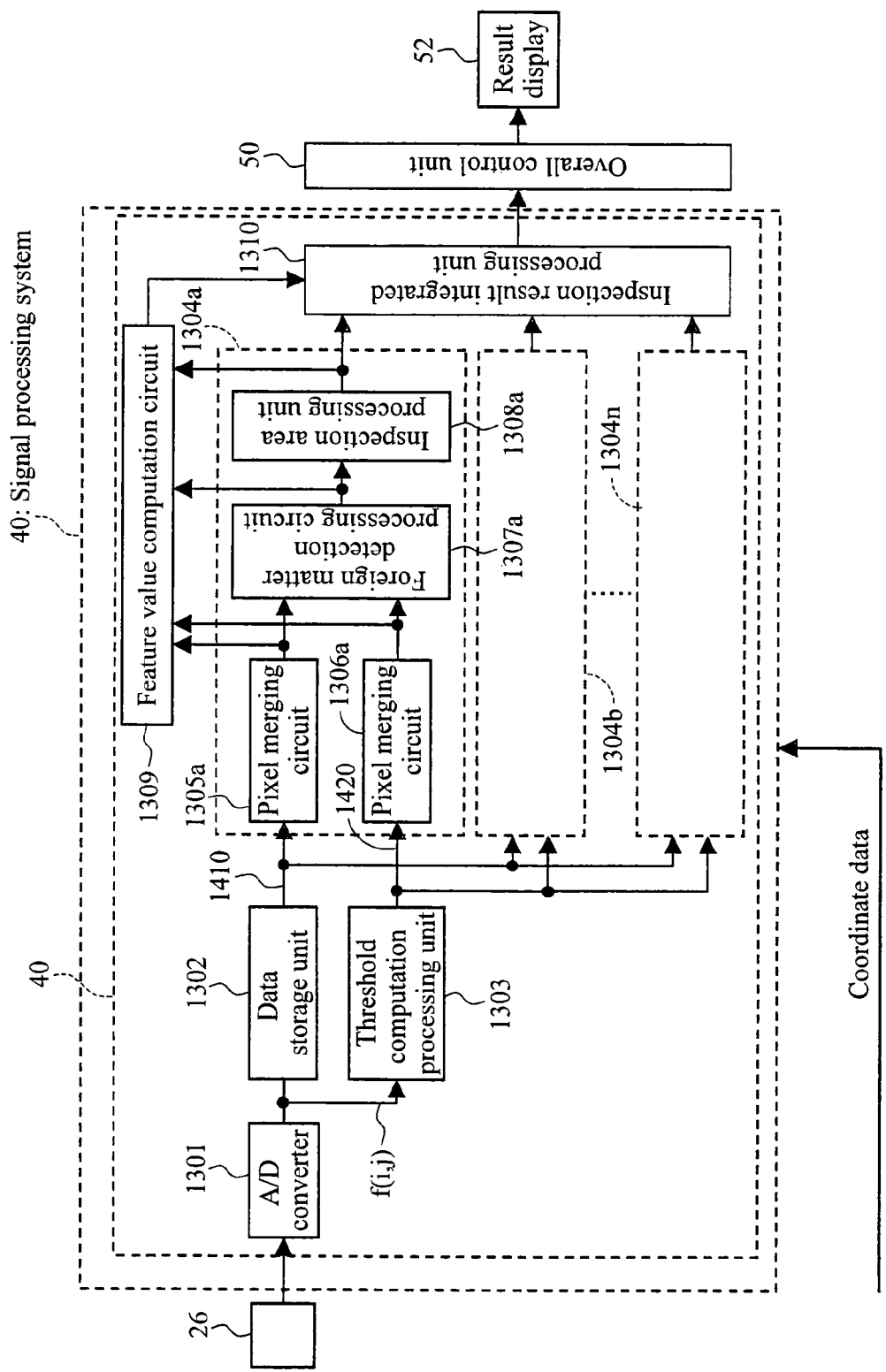
FIG. 12 is a block diagram showing a detailed configuration of a signal processing system of the first embodiment.

Then, detection signal processing in the inspection step (S2804) will be described. The signal processing system 40 processes the signal supplied from the photodetector 26 which accepts the diffraction light reflected from the surface of the wafer 1. FIG. 12 shows a configuration of the signal processing system 40.

The configuration and operation of the processing circuit 40 will be described with reference to FIG. 12. The processing circuit 40 includes an A/D converter 1301, a data storage unit 1302, a threshold computation processing unit 1303, and foreign matter detection processing units 1304a to 1304n. The A/D converter 1301 performs A/D conversion of the signal supplied from the photodetector 26. A detection image signal f(i,j) which has been A/D-converted is stored in the data storage unit 1302. The threshold computation processing unit 1303 performs threshold computation processing based on the detection image signal. The foreign matter detection processing units 1304a to 1304n include plural circuits which perform foreign matter detection processing per pixel merging based on both the detection image signal 1410 obtained from the data storage unit 1302 and a threshold image signal (Th(H), Th(Hm), Th(Lm), and Th(L)) 1420 obtained from the threshold computation processing unit 1303. The processing circuit 40 also includes a feature value computation circuit 1309 and an integrated processing unit 1310. The feature value computation circuit 1309 computes a scattered light quantity obtained from the defect by the low-angle illumination, a scattered light quantity obtained from the defect by the high-angle illumination, and a feature value such as the number of detected pixels indicating the spread of the defect. The integrated processing unit 1310 classifies defects on the wafer 1 into various kinds of defects such as the small and large foreign matters, the pattern defect, and the micro scratch, based on the feature value per merging obtained by the feature value computation circuit 1309.

Each of the foreign matter detection processing units 1304a to 1304n corresponds to each of 1×1, 3×3, ×5, . . . , n×n merging operators. The foreign matter detection processing units 1304a to 1304n include pixel merging circuits 1305a to 1305n and 1306a to 1306n, foreign matter detection processing circuits 1307a to 1307n, and inspection area processing units 1308a to 1308n, respectively.

The signal obtained by the photodetector 26 is converted into a digital signal by the A/D converter 1301, and the detection image signal f(i,j) 1410 is transmitted to the threshold computation processing unit 1303 while stored in the data storage unit 1302. The threshold computation processing unit 1303 computes the threshold image Th(i,j) 1420 for detecting the foreign matter, and the foreign matter detection processing circuit 1307 detects the foreign matter for each kind of merging operators based on the signals processed by the pixel merging circuit 1305 and 1306.

The detected foreign matter signal and threshold image are processed by the inspection area processing unit 1308 according to the detection position. At the same time, the feature value computation circuit 1309 computes the feature value (for example, the scattered light quantity obtained by the high-angle illumination, the scattered light quantity obtained by the low-angle illumination, and the number of pixels of the detected defect) based on the signals obtained from the pixel merging circuits 1305a to 1305n and 1306a to 1306n, the foreign matter detection processing circuits 1307a to 1307n, and the inspection area processing units 1308a to 1308n in the foreign matter detection processing units 1304a to 1304n each of which is provided for each kind of merging operators. Then, the integrated processing unit 1310 integrates the foreign matter signal and the feature value, and the integrated data is transmitted to the overall control unit 50.

The A/D converter 1301 has the function of converting the analog signal obtained by the photodetector 26 into the digital signal. Desirably the number of converted bits ranges from about 8 bits to about 12 bits. Because the resolution of the signal processing is lowered as the number of bits is decreased, the weak light is hardly detected. On the other hand, when the number of bits is increased, disadvantageously the apparatus becomes expensive.

The data storage unit 1302 is a circuit in which A/D-converted digital signal is stored.

The pixel merging circuits 1305 and 1306 will be described below. The pixel merging circuits 1305a to 1305n and 1306a to 1306n comprise their respective different merging operators.

Figure 13:
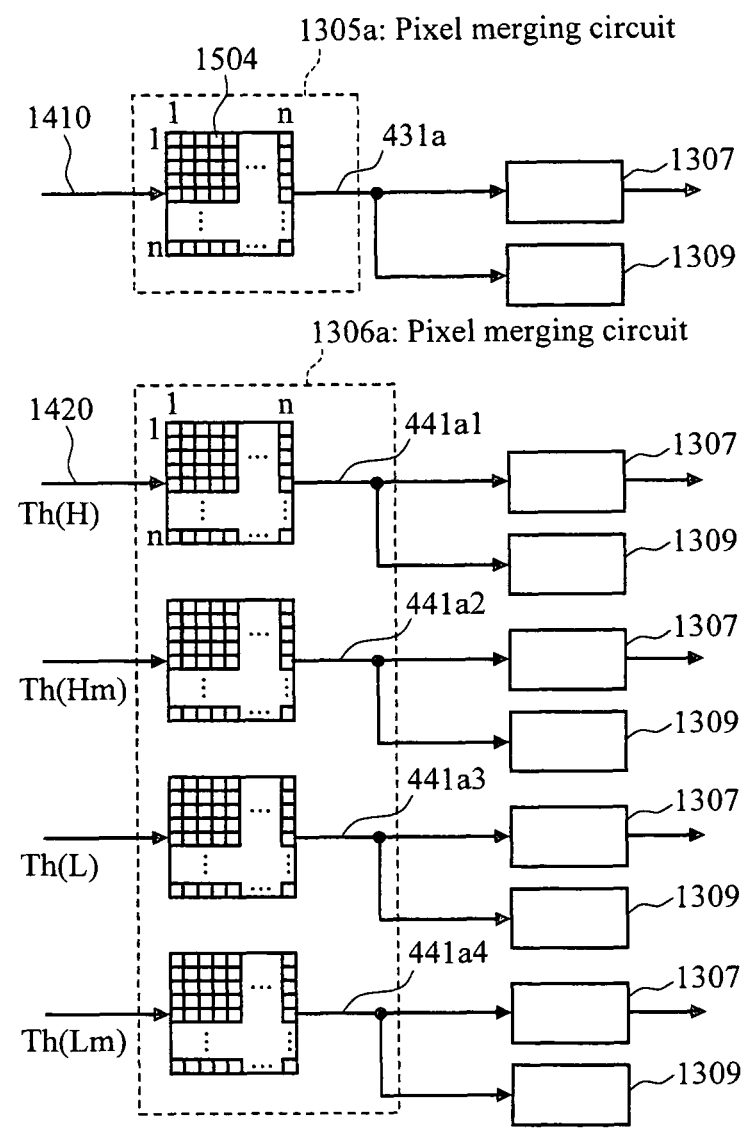
FIG. 13 is an explanatory view showing pixel merging circuits in the signal processing system of the invention.

As shown in FIG. 13, the merging operator has a function of merging the detection image signal f(i,j) 1410 obtained from the data storage unit 1302 and the differential threshold image signal 1420 obtained from the threshold computation processing unit 1303 in the range of the n×n pixels. The differential threshold image signal 1420 includes the detection threshold image Th(H), the detection threshold image Th(L), the verification threshold image Th(Hm), and the verification threshold image Th(Lm). For example, the merging operator is a circuit which yields an average of the n×n pixels.

At this point, the pixel merging circuits 1305a and 1306a comprise the merging operators which merge the 1×1 pixel, the pixel merging circuits 1305b and 1306b comprise the merging operators which merge the 3×3 pixels, and the pixel merging circuits 1305c and 1306c comprise the merging operators which merge the 5×5 pixels. Similarly, the pixel merging circuits 1305n and 1306n comprise the merging operators which merge the n×n pixels. The merging operator which merges the 1×1 pixel directly outputs the input signals 1410 and 1420.

Because the threshold image signal includes the four image signals (Th(H), Th(Hm), Th(Lm), and Th(L)) as described above, four merging operators Op are required in each of the pixel merging circuits 1306a to 1306n. Accordingly, the merging processing is performed to the detection image signals by various merging operators 1504, and the pixel merging circuits 1305a to 1305n supply the merging processing detection image signals 431a to 431n, respectively.

On the other hand, the merging processing is performed to the four threshold image signals (Th(H), Th(Hm), Th(Lm), and Th(L)) by various merging operators Op1 to Opn, and the pixel merging circuits 1306a to 1306n supply merging processing threshold image signals 441a (441a1 to 441a4) to 441n (441n1 to 441n4), respectively. The merging operators in the pixel merging circuits 1306a to 1306n are identical to one another.

The effect obtained by merging the pixels will be described below. In the foreign matter inspection, it is necessary to perform the detection without overlooking not only the micro foreign matter but also the large thin-film-like foreign matter spreading over a several-micrometer range. However, because the large detection image signal is not always obtained from the thin-film-like foreign matter, an S/N ratio is lowered in the detection image signal in units of pixel, and sometimes the thin-film-like foreign matter is overlooked. Therefore, the image is cut out in units of n×n pixels corresponding to the size of the thin-film-like foreign matter to be subjected to convolution operation, thereby improving the S/N ratio.

The inspection area processing units 1308a to 1308n will be described below. The inspection area processing units 1308a to 1308n are used for the foreign matter or defect detection signal which is obtained from the foreign matter detection processing circuits 1307a to 1307n while the chip is specified, in removing data of an area (also including an area in the chip) where the inspection is not required, in changing the detection sensitivity in each area (also including an area in the chip), or in selecting the area to be inspected.

In the inspection area processing units 1308a to 1308n, when the low detection sensitivity can be permitted in the area on the inspection target substrate 1, the threshold of the area obtained from the threshold computation unit of the threshold computation processing unit 1303 may be set at a higher level, or only the data of the foreign matter in the area to be inspected may be left from the pieces of data of the foreign matter supplied from the foreign matter detection processing circuits 1307a to 1307n based on the coordinate of the foreign matter.

The area where the low detection sensitivity can be permitted shall mean an area where the circuit pattern has a low density in the inspection target substrate 1. The advantage obtained by lowering the detection sensitivity is that the number of detected foreign matters is efficiently decreased. That is, sometimes several tens of thousands of foreign matters are detected in the high-sensitivity inspection apparatus. At this point, the foreign matter in the area where the circuit pattern exists is really significant, and the yield of the device production can be improved by dealing with the significant foreign matter.

However, when the whole area on the inspection target substrate 1 is inspected with the same sensitivity, the significant foreign matter cannot easily be extracted because the significant foreign matter and the insignificant foreign matter are mixed together. Therefore, in the inspection area processing units 1308a to 1308n, the detection sensitivity in the area which has a little influence on the yield because of the absence of the circuit pattern is lowered based on CAD information or threshold map information of the chip, so that the significant foreign matter can efficiently be extracted. In addition to the method for changing the detection sensitivity, the significant foreign matter may be extracted by classifying the foreign matters described below, or the significant foreign matter may be extracted based on the foreign matter size.

The feature value computation circuit 1309 will be described below. The feature value shall mean a value expressing the feature of the detected foreign matter or defect. The feature value computation circuit 1309 is a circuit which computes the feature value. Examples of the feature value include the diffraction light amount (scattered light quantity) (Dh,D1) reflected from the foreign matter or defect obtained by the high-angle illumination or low-angle illumination, the number of detected pixels, the shape or inertia major axis direction of the foreign matter detection area, the foreign matter detection site on the wafer 1, the kind of the underlying circuit pattern, and the threshold during the foreign matter detection.

The integrated processing unit 1310 will be described below. The integrated processing unit 1310 integrates foreign matter detection results processed in parallel by the pixel merging circuits 1305 and 1306, and the integrated processing unit 1310 integrates the feature value computed by the feature value computation circuit 1309 and the foreign matter detection result (positional information on the foreign matter defect) to transmit the integrated result to the overall control unit 50. Desirably the inspection result integrated processing is performed by a personal computer in order to facilitate the change in processing contents.

On the other hand, the TV camera 92 takes the diffraction light image reflected from the repetitive pattern formed in the wafer 1 at the image formation position of the Fourier transform image of the detection optical system 20. The image signal of the bright spots of the diffraction light image is transmitted to the signal processing circuit 95, converted into the digital signal by the A/D converter of the signal processing circuit 95, and processed as the image data by the image data processing unit of the signal processing circuit 95.

In the signal processing circuit 95, the signal processed as the image data by the image data processing unit is transmitted to a pattern pitch operating unit to obtain a pitch between the bright spots of the diffraction light image. The obtained data of the pitch between the bright spots and the image data are transmitted from the signal processing circuit 95 to the overall control unit 50, and the pitch data and the image data are transmitted to the spatial filter control unit 27 in order to control the array pitch between light shielding plates of the spatial filter 22.

Thus, in the first embodiment of the invention, the wafer 1 placed on the placement table 34 is covered with the foreign matter anti-adhesive means 180 having the transparent plate 187, and the surface of the wafer 1 is irradiated with the light through the transparent plate 187 to detect the scattered light, thereby detecting the foreign matter and defect on the surface of the wafer 1.

Accordingly, the contamination particles generated by the defect inspection operation is prevented from adhering to the surface of the wafer 1, thereby realizing the defect inspection method and apparatus in which the micro foreign matter or defect can accurately be inspected at a high speed.

Additionally, the foreign matter is also inspected in the backside of the wafer 1, and the foreign matter is removed when detected in the backside.

Therefore, the foreign matter can be prevented from adhering to surfaces of other wafers from the backside of the wafer 1.

Second Embodiment

A second embodiment of the invention will be described below. In the foreign matter inspection, it is necessary to inspect a multi-layer wafer in which a transparent film (for example, oxide film) is formed in the surface of the wafer 1. The multi-layer wafer is formed by repeating a process for forming a pattern on the transparent film. The needs for detecting only the foreign matter in the surface of the oxide film are grown in the foreign matter inspection on the wafer 1 in which the transparent film such as the oxide film is formed.

Basically the influence of the light reflected from the underlying layer such as the pattern diffraction light can be restricted to a lower level by decreasing the illumination angle α. However, regular reflection of the illumination light, that is, the forward scattered light is increased in the scattered light generated from the foreign matter by decreasing the illumination angle α, and the small quantity of scattered light is incident to the detection optical system provided above, which causes a problem in that the foreign matter cannot stably be detected.

Figure 10A:
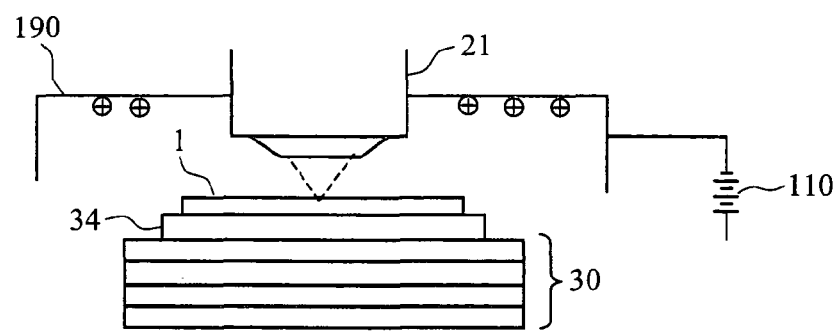
FIGS. 10A and 10B are explanatory views showing a main part of a defect inspection apparatus according to a second embodiment of the invention.
Figure 10B:
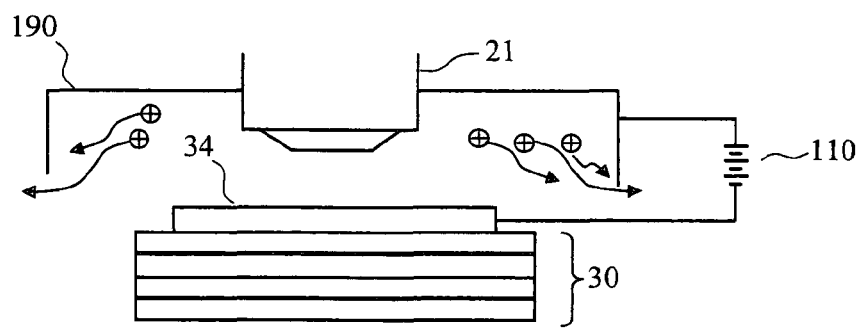

Therefore, in the second embodiment of the invention, as shown in FIGS. 10A and 10B, a dielectric member 190 is provided above the wafer 1, and the dielectric member 190 is charged in the polarity opposite to that of the foreign matter to tentatively trap the floating particles in the inspection apparatus.

In FIG. 10A, a power supply 110 negatively charges the dielectric member 190, and the positive particles are retained by the dielectric member 190. In the case where the wafer 1 is not placed on the placement table 34, as shown in FIG. 10B, the polarity of the dielectric member 190 is changed to the positive polarity to remove the positively-charged particles at once. At this point, it is effective that ionized air is flown and that at the same time, the air is exhausted from left and right directions below the conveyance system 30. The overall control unit 50 controls the operation of the power supply 110.

The first embodiment differs from the second embodiment in the anti-adhesive means which prevents the contamination particles from adhering to the surface of the wafer 1. That is, the transparent plate 187 with which the wafer 1 is covered is provided in the first embodiment while the dielectric member 190 which traps the contamination particles is provided in the second embodiment. Because other configurations in the second embodiment are similar to those in the first embodiment, the description will not be repeated here.

The effect similar to that of the first embodiment can be obtained in the second embodiment.

Third Embodiment

Figure 11A:
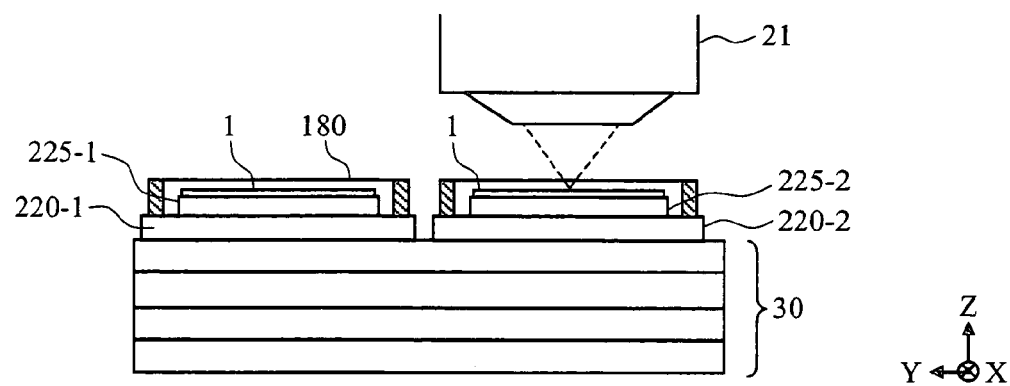
FIGS. 11A and 11B are explanatory views showing a main part of a defect inspection apparatus according to a third embodiment of the invention.

Then, a third embodiment of the invention will be described. In the third embodiment, as shown in FIGS. 11A and 11B, the different kinds of the wafers 1 can be placed on the conveyance system 30, and two placement tables including wafer chucks 225-1 and 225-2 and chuck holders 220-1 and 220-2 are provided on the conveyance system 30 of the defect inspection apparatus.

In the defect inspection apparatus, when the wafer in which a metal film is formed and the wafer in which the metal film is not formed are inspected, it is necessary to perform work for exchanging the dedicated chucks. Therefore, in the third embodiment, the different chucks 225-1 and 225-2 are provided to shorten the time for exchanging the chucks, and the chucks 225-1 and 225-2 are separately used according to the usage.

Figure 11B:
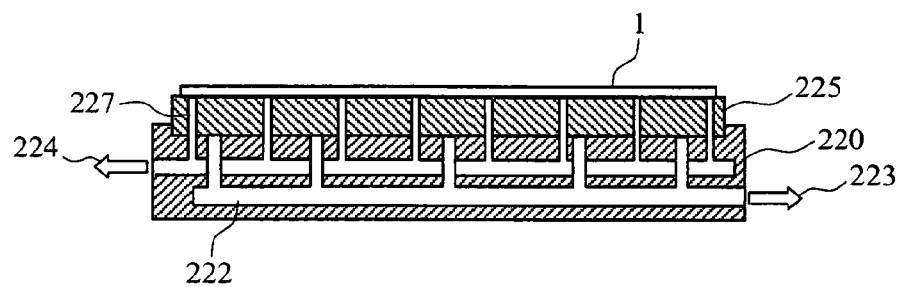

As shown in FIG. 11B, the wafer chuck 225 (225-1 and 225-2) on which the wafer 1 is mounted is fixed by performing evacuation in a direction indicated by an arrow 223 through plural chuck adsorption holes 222 made in a chuck holder 220 (220-1 and 220-2). The wafer 1 is adsorbed by performing evacuation in a direction indicated by an arrow 224 through plural wafer adsorption holes 227 made in the wafer chuck 225.

Both the wafer chuck 225 and the chuck holder 220 are covered with the foreign matter anti-adhesive means 180, and opening and closing mechanisms of the foreign matter anti-adhesive means 180 are similar to that of FIGS. 6A and 6B.

The backside foreign matter inspection apparatus 155 is also applied to the third embodiment. Accordingly, in inspecting the backside of the wafer 1, when the number of detected foreign matters is not lower than a reference value, it is determined that the wafer adsorption surface of the wafer chuck 225 is contaminated, and a warning about the exchange of the wafer chuck is issued. The warning is displayed on the display means 52 under the control of the overall control unit 50.

Because other configurations in the third embodiment are similar in those of the first embodiment, the description will not be repeated here.

The effect similar to that of the first embodiment can be obtained in the third embodiment. In addition, advantageously the work for exchanging the dedicated wafer chucks can be eliminated in the case when the wafer in which the metal film is formed and the wafer in which the metal film is not formed are inspected.

In the third embodiment, the wafer chuck 225 and the chuck holder 220 are covered with the foreign matter anti-adhesive means 180. Alternatively, the dielectric member 190 of FIGS. 10A and 10B may be disposed instead of the foreign matter anti-adhesive means 180 of FIGS. 6A and 6B.

Fourth Embodiment

Figure 14:
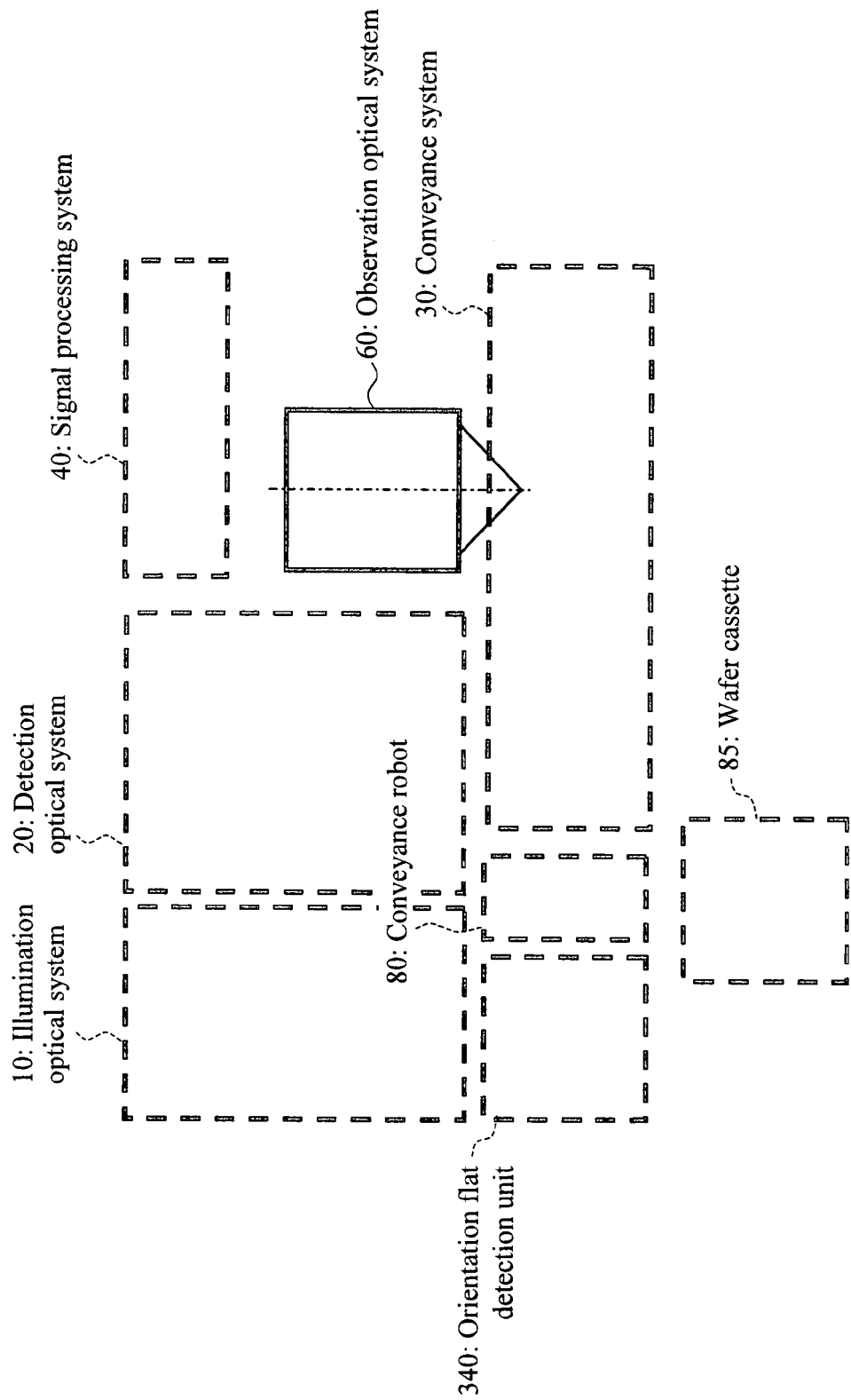
FIG. 14 is a schematic diagram showing a configuration of a defect inspection apparatus according to a fourth embodiment of the invention.

A fourth embodiment of the invention will be described below. In the fourth embodiment, a microscope is attached to the defect inspection apparatus. FIG. 14 shows a schematic configuration of a defect inspection apparatus of the fourth embodiment. Because the basic configuration of the fourth embodiment is similar to that of the first embodiment, only the layout is shown in FIG. 14 for the sake of simple illustration.

As shown in FIG. 14, in the fourth embodiment, the observation optical system 60 can confirm the foreign matter detected by the inspection. That is, the microscope is provided in the observation optical system 60. In the observation optical system 60, the stages 31 and 32 are moved to move the foreign matter (including the misinformation) detected on the wafer 1 to a visual field position of the microscope of the observation optical system 60, and the image of the foreign matter is observed.

The effect similar to that of the first embodiment can be obtained in the fourth embodiment. Additionally, the following effects can also be obtained in the fourth embodiment.

The advantage obtained by providing the observation optical system 60 is that the detected foreign matter can instantaneously be observed without moving the wafer 1 to a review device such as SEM. The object detected by the inspection apparatus can instantaneously be observed to quickly specify a generation factor of the foreign matter. The foreign matter image taken by the TV camera 64 of the observation optical system 60 is displayed on a color monitor shared by the personal computer, the laser irradiation and the stage scanning can partially be performed with a central focus on the coordinate of the detected foreign matter, and the scattered light image of the foreign matter and the foreign matter position can be marked and displayed on the monitor.

Therefore, it can be confirmed whether or not the foreign matter is actually detected. In the partial image obtained by the stage scanning, because an inspection image of a die adjacent to a die in which the foreign matter is detected can be obtained, the comparison and confirmation can be made on site.

In the microscope of the observation optical system 60, visible light (for example, white light) or an ultraviolet ray may be used as the light source. Particularly, the high-resolution microscope such as the one in which the ultraviolet ray is used is desirable in order to observe the micro foreign matter. Advantageously the use of the visible-light microscope obtains color information on the foreign matter to easily recognize the foreign matter.

In the first embodiment of the invention, the foreign matter anti-adhesive means 180 is turned about the shaft 181 to cover the wafer 1 or to uncover the wafer 1. However, the wafer 1 may be covered and uncovered by another method. For example, a member which is opened and closed may be formed in a side surface portion of the foreign matter anti-adhesive means. The foreign matter anti-adhesive means is slid to cover the wafer 1 while the opening and closing member is opened, and the inspection is performed after the opening and closing member is closed. Then, after the opening and closing member is opened, the foreign matter anti-adhesive means is slid to uncover the wafer 1.

The foreign matter anti-adhesive means 180 can be configured to be replaced for new one. The foreign matter anti-adhesive means 180 may periodically be replaced. A unit which senses a degree of dirty of the foreign matter anti-adhesive means 180 is provided, and the display means 52 can indicate that the replacement is required when the degree of dirty is not lower than a predetermined value.

A cabinet is provided to store the plural foreign matter anti-adhesive means, and the foreign matter anti-adhesive means 180 can automatically be replaced.

The wafer chuck may be configured to be periodically cleaned. That is, a dummy wafer is placed on the placement table 34, and the wafer chuck can be cleaned with the dummy wafer.

What is claimed is:
1. A defect inspection apparatus comprising:
a light source;
a placement table for mounting a sample;
a moving unit which moves said placement table;
an irradiation unit for irradiating the sample placed on the placement table with light emitted from the light source;

a light detection unit for detecting light reflected from a sample surface;
a defect detection unit for detecting a defect on the sample surface based on the reflected light detected by the light detection unit;
a foreign matter anti-adhesive unit for preventing a foreign matter from adhering to the surface of the sample, wherein:
the foreign matter anti-adhesive unit covers the sample;
an opening-closing unit for opening and closing the foreign matter anti-adhesive unit in a direction along a z-direction of said sample, said z-direction being the direction perpendicular to the plane of the placement table; and
a convey system which conveys the sample associated with said opening-closing unit;
the foreign matter anti-adhesive unit is attached to the opening-closing unit, and the opening-closing unit is arranged on the moving unit, and
the foreign matter anti-adhesive unit is formed of a dielectric member, said dielectric member being charged by an electric source in a polarity opposite to a foreign matter for trapping the foreign matter on the dielectric member.

2. The defect inspection apparatus according to claim 1, comprising a backside foreign matter inspection unit for inspecting whether or not the foreign matter adheres to a backside of the sample.

3. The defect inspection apparatus according to claim 2, comprising a foreign matter removal unit for removing the foreign matter adhering to the backside of the sample when the backside foreign matter inspection unit determines that the foreign matter adheres to the backside.

4. The defect inspection apparatus according to claim 2, comprising:
a display unit; and
a control unit for controlling display of the display unit,
wherein the control unit causes the display unit to display that the placement table is contaminated when the number of foreign matters detected by the backside foreign matter inspection unit is not lower than a predetermined value.

5. The defect inspection apparatus according to claim 1, comprising two placement tables,
wherein the placement tables are provided so as to correspond to different kinds of samples, and the foreign matter anti-adhesive unit is disposed for each of the placement tables.

6. The defect inspection apparatus according to claim 1, comprising an observation optical unit for confirming the defect.

7. The defect inspection apparatus according to claim 1, further comprising a supply unit for supplying an ionized-air to the foreign matter anti-adhesive unit.

8. A defect inspection method comprising:
irradiating a surface of a sample placed on a placement table with light;
moving the placement table by a moving unit;
detecting light reflected from the sample surface; and
detecting a defect on the sample surface,
wherein the defect of the sample surface is detected by irradiating the sample surface with the light, while a foreign matter anti-adhesive unit prevents a foreign matter from adhering to the surface of the sample; wherein
the foreign matter anti-adhesive unit covers the sample;
an opening-closing unit opens and closes the foreign matter anti-adhesive unit in a Z-direction of said sample, said z-direction being the direction perpendicular to the plane of the placement table; and
a convey system conveys the sample associated with said opening-closing unit; and
wherein the foreign matter anti-adhesive unit is attached to the opening-closing unit, and the opening-closing unit is arranged on the moving unit, and
the foreign matter anti-adhesive unit is formed of a dielectric member, said dielectric member being charged by an electric source in a polarity opposite to a foreign matter for trapping the foreign matter on the dielectric member.

9. The defect inspection method according to claim 8, wherein a transparent plate which transmits the light is moved above the surface of the sample placed on the placement table, thereby preventing the foreign matter from adhering to the surface of the sample.

10. The defect inspection method according to claim 8, comprising inspecting whether or not the foreign matter adheres to a backside of the sample.

11. The defect inspection method according to claim 10, comprising removing the foreign matter adhering to the backside of the sample when it is determined that the foreign matter is adhering to the backside.

12. The defect inspection method according to claim 10, comprising issuing a warning that the placement table is possibly contaminated when the number of foreign matters detected in the backside of the sample is not lower than a predetermined value.

13. The defect inspection method according to claim 9, comprising confirming the detected foreign matter with an observation optical unit when the defect is detected on the sample surface.

14. The defect inspection method according to claim 8, wherein an ionized-air is supplied to the foreign matter anti-adhesive unit by a supply unit.

15. An inspection apparatus comprising:
a mount unit for mounting a substrate;
a dielectric member; and
a power supply for connecting said mount unit with said dielectric member electrically,
wherein said power supply supplies electric voltage to said dielectric member and said mount unit, and
wherein said dielectric member is charged by said power supply in a polarity opposite to a foreign matter for trapping the foreign matter on said dielectric member.

16. The inspection apparatus according to claim 15, wherein said power supply changes direction of electric voltage as a function of existence of said substrate on said mount unit.

17. The inspection apparatus according to claim 16, further comprising an exhaust unit for exhausting air surrounding said mount unit.

18. The inspection apparatus according to claim 17, further comprising a supply unit for supplying ionized air to a space between said mount unit and said dielectric member.

19. A method for inspection comprising:
mounting a substrate on a mount unit;
connecting the mount unit with a dielectric member electrically via a power supply,
supplying electric voltage to said a dielectric member and said mount unit with the power supply,
charging said dielectric member by said power supply in a polarity opposite to a foreign matter located on the substrate,
trapping the foreign matter on said dielectric member, and inspecting the substrate.

20. The method according to claim 19, wherein said power supply changes a direction of electric voltage as a function of existence of said substrate on said mount unit.

21. The method according to claim 20, further comprising a step of exhausting air surrounding said mount unit.

22. The method according to claim 21, further comprising a step of supplying ionized air to a space between said mount unit and said dielectric member via a supply unit.

* * * * *